United States Patent
Ito et al.

(10) Patent No.: US 6,858,182 B1
(45) Date of Patent: Feb. 22, 2005

(54) EXHALATION GASEOUS COMPONENT GAUGE AND A CELLULAR PHONE EQUIPPED WITH FUNCTION OF MEASURING GASEOUS COMPONENTS

(75) Inventors: Yusuke Ito, Tokyo (JP); Kuniyoshi Koizumi, Tokyo (JP); Hiroki Kenmochi, Tokyo (JP)

(73) Assignee: Tanita Corporation, Tokyo (JP)

( * ) Notice: Subject to any disclaimer, the term of this patent is extended or adjusted under 35 U.S.C. 154(b) by 0 days.

(21) Appl. No.: 09/551,349

(22) Filed: Apr. 18, 2000

(30) Foreign Application Priority Data

Apr. 23, 1999 (JP) .......................................... 11/115600
May 28, 1999 (JP) .......................................... 11/149405

(51) Int. Cl.[7] ............................................. G01N 21/00
(52) U.S. Cl. .............................. 422/58; 422/83; 422/84; 422/86; 422/61; 340/870.28
(58) Field of Search ............................. 422/83, 58, 84, 422/86, 61, 55, 88, 98; 340/870.28

(56) References Cited

U.S. PATENT DOCUMENTS 4,823,803 A    4/1989   Nakamura
5,157,601 A  * 10/1992   Jones et al. ............. 364/413.11
5,571,395 A  * 11/1996   Park et al. ................... 204/403
6,396,416 B1 *  5/2002   Kuusela et al. ......... 340/870.28

FOREIGN PATENT DOCUMENTS

| EP | 0885591 A2 | 12/1998 |
|---|---|---|
| JP | 62157572 | 7/1987 |
| JP | 4-15063 | 2/1992 |
| JP | 5-28324 | 4/1993 |
| JP | 5-322816 | 12/1993 |
| WO | WO93/12604 | 6/1993 |

* cited by examiner

*Primary Examiner*—Jill Warden
*Assistant Examiner*—Sam P. Siefke
(74) *Attorney, Agent, or Firm*—McDermott, Will & Emery

(57) ABSTRACT

Disclosed is an exhalation gaseous component gauge including, in a palm-sized casing having exhalation taking-in and taking-out slots made on its front and rear sides, a semiconductor gas sensor so placed that the air flowing from one's mouth may pass the sensor, a CPU responsive to the signal from the sensor for determining the quantity of the exhalation gaseous components, and a display for showing the so determined result. The palm-sized casing is so sized and configured as to permit one to have a look at the display while holding the gauge in hand to direct the air from the mouth to the exhalation taking-in slot. Also, disclosed is a cellular phone equipped with an exhalation gaseous component gauge.

12 Claims, 8 Drawing Sheets

(a)

(b)

(c)

(d)

(e)

(f)

(g)

(h)

(a)

(b)

(c)

(d)

(e)

(f)

(g)

(h)

US 6,858,182 B1

EXHALATION GASEOUS COMPONENT GAUGE AND A CELLULAR PHONE EQUIPPED WITH FUNCTION OF MEASURING GASEOUS COMPONENTS

BACKGROUND OF THE INVENTION

1. Field of the Invention

The present invention relates to an exhalation gaseous component gauge and a cellular phone equipped with function of measuring gaseous components, and more particularly to such a gauge and cellular phone for giving an indication of the degree of smelling bad in someone's breath or giving an indication of the degree of intoxication.

2. Prior Arts

The main cause for bad breath is the producing of volatile sulfide from bacteria plaque in mouth, where bacillus is allowed to be active at the surrounding temperature about one degree C. higher than the body temperature. The bad breath is said to be composed of hydrogen sulfide ($H_2S$) and methyl mercaptan ($CH_3SH$). The degree of bad smell depends on individual factors, such as age, physical condition, length of time subsequent to teeth brushing or taking foods, diseases in mouth or emission of saliva. Even though the degree of smelling bad in someone's breath is strong enough to be noticeable to others, it is likely that the unpleasing smell is unnoticed of by the person whose breath smells bad. There has been, therefore, a demand for permitting one to measure readily the degree of bad smell in his breath, if any.

To meet such a demand an exhalation gaseous component gauge was proposed in Japanese Utility Model Registration Application, Laid-Open No.5-28324, and such breath gauges have been used by those who are anxious about their breath or are suffering from periodontal disease. The breath gauge uses a semiconductor gas sensor which is sensitive to some selected gaseous components in one's exhalation for giving an indication of the degree of smelling bad in his breath. When the power switch turns "on", the breath sensor is heated to be cleaned, and then, it responses to one's breath blowing over the sensor for determining the amount of odor components, and finally, the measuring result is displayed in the form of graphic and alphanumeric representation.

People want to drink alcohol for relaxation. A significant relation, however, is observed between the amount of drinking alcohol and the hepatocirrhosis, and between the alcohol-drinking amount and the alcoholic dependency. The alcohol-drinking amount, therefore, should be limited to the extent that one's mind is relaxed. There has been, therefore, a demand for permitting one to measure readily the degree of intoxication.

To meet such a demand an exhalation gaseous component gauge was proposed in Japanese Utility Model Registration Application, Laid-Open No.4-15063. The breath gauge uses a semiconductor gas sensor which is sensitive to alcohol in one's exhalation for giving an indication of the degree of intoxication. When the power switch turns "on", the breath sensor is heated to be thermally cleaned, and then, it responses to one's breath blowing over the breath sensor for determining the alcoholic amount therein, and finally, the measuring result is given in some liquid crystal displays, each representing a particular drinking amount when lit.

The breath gauges as described above may use different semiconductor sensors appropriate for the purposes, which are capable of detecting some selected gaseous components in one's breath such as methyl mercaptan, ethyl alcohol etc.

Usually one is anxious about his breath during conversation or after a meal. In this connection the breath gauge is preferably so sized as to permit one to carry with him everywhere and to make a breath test readily without being noticeable to others. The conventional breath gauge, however, is equipped with a relatively large-sized liquid crystal display device, which is capable of giving alphanumeric and graphic indications of odor degree, and an extra display showing the remaining length of time for the standby condition for measurement. The size of the breath gauge is accordingly large, preventing one from carrying the gauge with him and from making a breath test without being noticed by others.

As for the intoxication gauge one who is drinking alcohol wants to make a breath test, and it is preferable to realize at a first glance, how much he has been intoxicated.

Inconveniently the conventional breath gauge structure does not permit one to look at the display while he is putting his mouth close to the sensor to blow his breath thereto. This position prevents him to confirm that the testing is being made in correct position by keeping the display watched for the while. As a result the person is often compelled to repeat the breath test.

SUMMARY OF THE INVENTION

In view of the above one object of the present invention is to provide an exhalation gauge which is so small-sized and configured as to permit one to carry it with him and make a breath test while watching the proceeding of the test without being noticed by others, permitting him to realize the breath test result at a glance.

To attain this object an exhalation gaseous component gauge including, in a palm-sized casing having exhalation taking-in and taking-out slots made on its front and rear sides respectively, at least an electric power supply, a CPU connected to the power supply via an associated switch, a gas sensor connected to the CPU and a display device fixed to the front side of the casing, and connected to the CPU, is improved according to the present invention in that the gas sensor being so placed as to permit the breath out of one's mouth to flow over the gas sensor on the way from the exhalation taking-in slot to the exhalation taking-out slot, the palm-sized casing being so sized and configured as to permit one to have a look at the display while holding the gauge in hand to direct the breath from one's mouth to the exhalation taking-in slot.

The exhalation gaseous component gauge may include further a buzzer connected to the CPU, thus permitting the buzzer to respond to detection of the exhalation by the gas sensor for informing a person of detection of the exhalation.

The CPU may be so programmed as to permit the display to show pictures varying with the detected component quantities.

The gas sensor may have halitosis-sensitive characteristics, thereby giving an indication of the degree of smelling bad in someone's breath.

The pictures may show countenances varying with the detected component quantities.

The gas sensor may have alcohol-sensitive characteristics, thereby giving an indication of the degree of intoxication.

The pictures may show the remaining liquid amount in a glass and/or countenances or postures varying with the detected component quantities.

The CPU may be so programmed as to permit the display device to in give graphic representations of the length of time left for the gauge to reach the standby position for measurement.

The gas sensor may be a semiconductor gas sensor, but any other appropriate gas sensor may be used.

Another object of the present invention is to provide a cellular phone equipped with function of measuring exhalation gaseous components.

To attain this object a cellular phone equipped with function of measuring exhalation gaseous components according to the present invention is characterized in that a palm-sized casing has exhalation taking-in and taking-out slots made on its front and rear sides respectively, and that a gas sensor is so placed in the casing as to permit the breath out of one's mouth to flow over the gas sensor on the way from the exhalation taking-in slot to the exhalation taking-out slot, the CPU of the cellular phone being connected to the gas sensor, and being so programmed as to determine the quantity of the exhalation gaseous components detected by the sensor and to allow the display device of the cellular phone to show the so determined quantity of the exhalation gaseous components.

The cellular phone may include further a buzzer connected to the CPU, thus permitting the buzzer to respond to detection of the exhalation by the gas sensor for informing a person of detection of the exhalation.

The CPU may be so programmed as to permit the display device to show pictures varying with the detected component quantities.

The gas sensor may have halitosis-sensitive characteristics, it thereby giving an indication of the degree of smelling bad in someone's breath.

The pictures may show countenances varying with the detected component quantities.

The gas sensor may have alcohol-sensitive characteristics, thereby giving an indication of the degree of intoxication.

The pictures may show the remaining liquid amount in a glass and/or countenances or postures varying with the detected component quantities.

The CPU may be so programmed as to permit the display device to give graphic representations of the length of time left for the gauge to reach the standby position for measurement.

The gas sensor may be a semiconductor gas sensor, but an appropriate gas sensor other than the semiconductor gas sensor may be used.

BRIEF DESCRIPTION OF DRAWINGS

FIG. 2(a) is a front view of the exhalation gaseous component gauge designed for measuring the degree of unpleasant mouth odor whereas

FIG. 4(a) is a front view of the exhalation gaseous component gauge designed for measuring the degree of intoxication whereas

FIG. 7(a) is a front view of the cellular phone equipped with function of measuring the degree of unpleasant odor whereas

DESCRIPTION OF PREFERRED EMBODIMENTS

Figure 1:
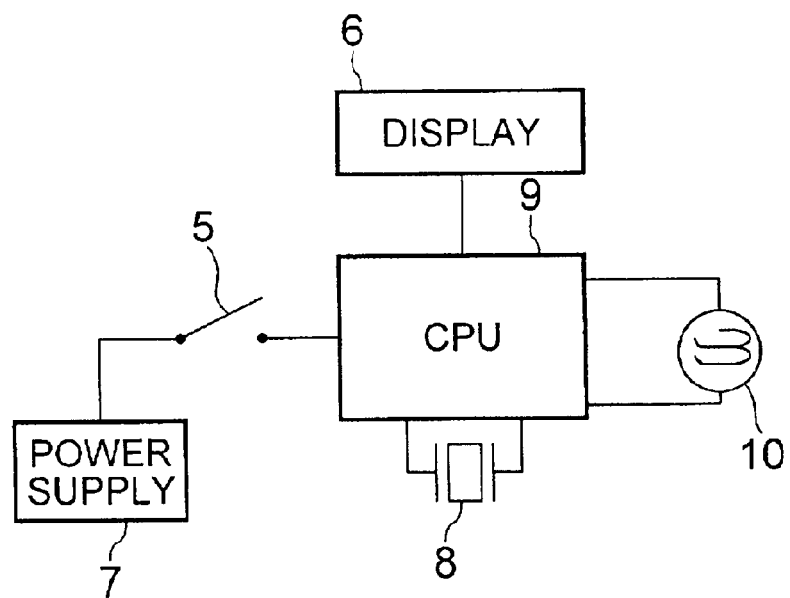
FIG. 1 is a block diagram showing an exhalation gaseous component gauge according to the present invention.
Figure 2A:
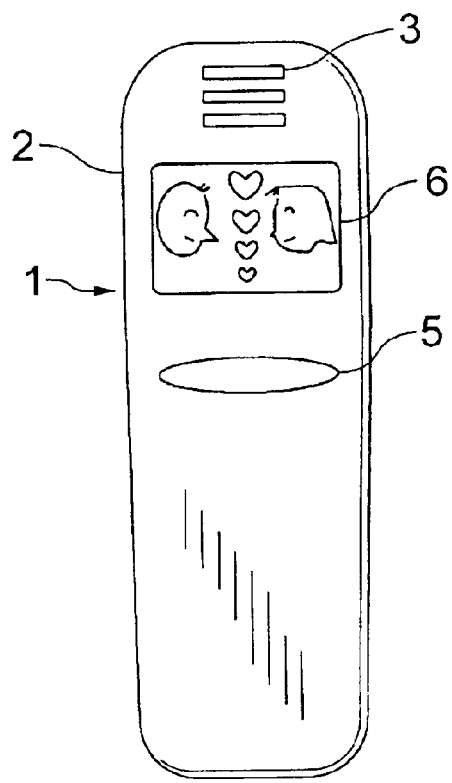
Figure 2B:
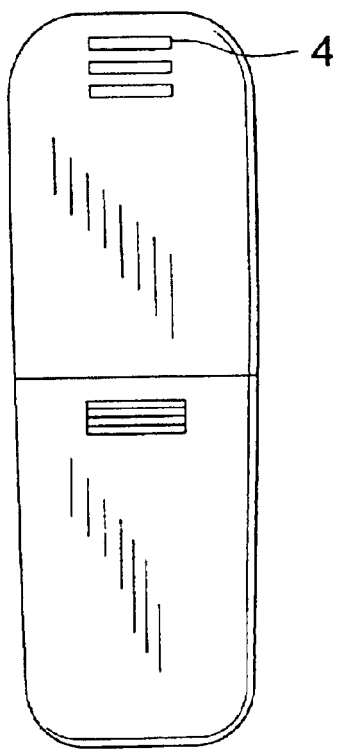
FIG. 2(b) is a rear view of the breath gauge.

Referring to FIGS. 1 and 2, an exhalation gaseous component gauge is described as being applied to measuring the degree of unpleasant odor or bad breath. It has a palm-sized casing 2, which has exhalation taking-in and taking-out slots 3 and 4 made on its front and rear sides respectively. A display device 6 is fixed to the front side of the casing 2, and a switch 5 appears on the front side. As seen from FIG. 1, the breath gauge 1 includes, in its palm-sized casing 2, an electric power supply 7, a CPU 9 connected to the power supply 7 via the switch 5, a semiconductor gas sensor 10 connected to the CPU 9 and a buzzer 8 connected to the CPU 9. The CPU 9 can perform required arithmetic operation and control. The semiconductor gas sensor 10 is so placed as to permit the breath out of one's mouth to flow over the semiconductor gas sensor 10 on the way from the exhalation taking-in slot 3 to the exhalation taking-out slot 4. As seen from FIG. 2, the palm-sized casing 2 is so sized and configured as to permit one to have a look at the display 6 while holding the breath gauge 1 in hand to direct the breath from one's mouth to the exhalation taking-in slot 3.

The display device 6 gives graphic representations showing the result of measurement, the length of time left for putting the gauge 1 in its standby condition for measurement, the remaining quantity of electricity available from the battery and other useful pieces of information.

The halitosis-sensitive semiconductor gas sensor 10 for indicating the degree of smelling bad in someone's breath is a ceramic insulator body coated with a semiconductor material of tin oxide ($SnO_2$), and the ceramic insulator body has a heater coil contained therein. Japanese Patent Application Laid-Open No.1-35368 describes such a semiconductor gas sensor in detail.

The buzzer 8 responds to detection of the exhalation by the semiconductor gas sensor 10 for informing the user of detection of the exhalation. The CPU 9 are so programmed as to permit the display 6 to show pictures varying with the detected component quantities as described later in detail.

Figure 3:
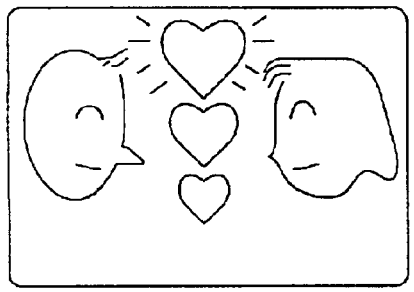
FIGS. 3(a) to (h) are graphic representations showing what different pictures appear to indicate the increasing degree of unpleasant odor.
Figure 3:
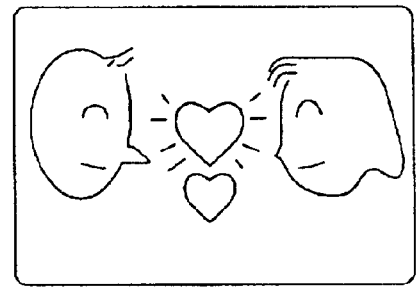
Figure 3:
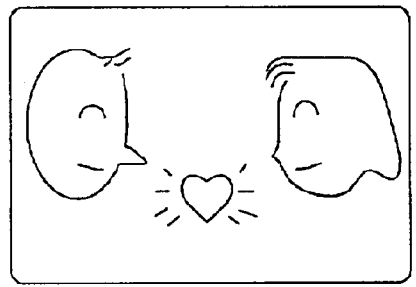
Figure 3:
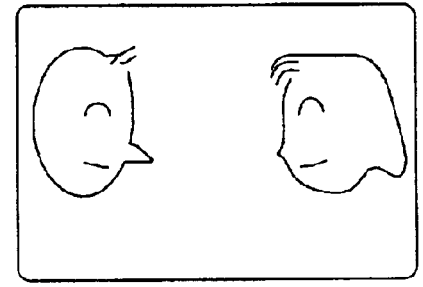
Figure 3:
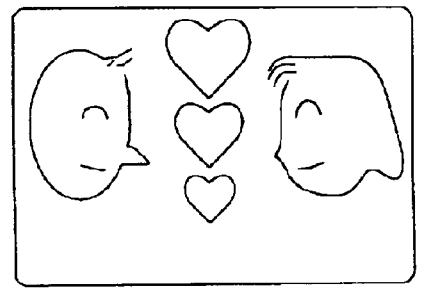
Figure 3:
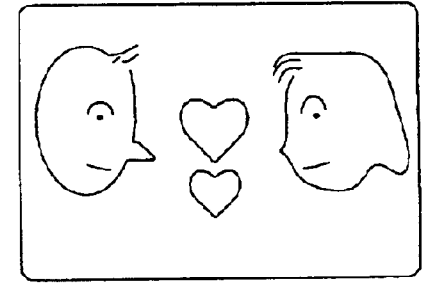
Figure 3:
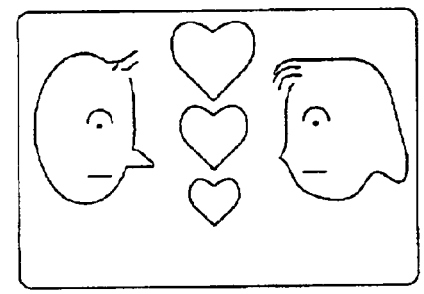
Figure 3:
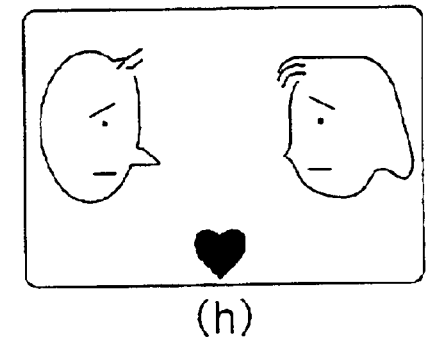

The manner in which the breath gauge 1 is used is described below:

First, the power switch 5 is depressed to put the power supply 7 in circuit with the components of the breath gauge 1, and then, man's and woman's faces and three heart marks appear on the display 6 (see FIG. 3a). At the same time, a voltage is applied across the heater coil of the semiconductor gas sensor 10, thus effecting the thermal cleaning of the semiconductor gas sensor 10 and keeping it at a given constant temperature (standby condition for measurement). In the display the number of the heart marks decreases with time, showing the length of time left for reaching the standby condition (see FIGS. 3a, 3b and 3c), and finally no heart mark appears, thus leaving two smiling faces on the display 6 at the time of finishing the thermal cleaning of the semiconductor sensor 10 (see FIG. 3d). Then, the user puts the breath gauge 1 close to his mouth to blow a breath into the exhalation taking-in slot 3.

The buzzer 8 responds to the signal from the semiconductor gas sensor 10 for making a continuous sound, thereby informing the user of the finishing of the required measurement. The mixture gas of methyl mercaptan and ethylene in the breath is deposited on the heated semiconductor gas sensor 10 to be burnt there, thus reducing the electric resistance of the semiconductor gas sensor 10 to increase the electric current flowing in the CPU 9 accordingly. The CPU 9 makes a required calculation of the concentration of the mixture gas by comparing the increased quantity of electric current with a set reference value, and then, the CPU 9 shows the resultant of calculation on the display 6. The degree of foul breath is indicated in terms of segments selected in the display 6.

Referring to FIGS. 3(e) to 3(h), the concentration of the unpleasant mixture gas relative to the breath ranging from 0 to 0.19 ppm (no significant foul breath) is indicated in terms of three heart marks (see FIG. 3e); the concentration of the unpleasant mixture gas ranging from 0.2 to 0.29 ppm (noticeable foul breath) is indicated in terms of two heart marks (see FIG. 3f); the concentration of the unpleasant mixture gas ranging from 0.3 to 0.49 ppm (significant foul breath) is indicated in terms of one heart mark (see FIG. 3g); and the concentration of the unpleasant mixture gas beyond 0.5 ppm (strong foul breath) is indicated in terms of black heart mark (see FIG. 3h). Accordingly the faces wear smile less and less.

The indication will automatically disappear in several seconds, thus finishing the measurement. If the battery is being exhausted, four heart marks appear and disappear in response to depression of the power switch 5, thus informing the user of shortage of electricity in the battery. Graphic representations other than heart marks and countenances of young man and woman may be used, such as bar graphs.

Figure 4A:
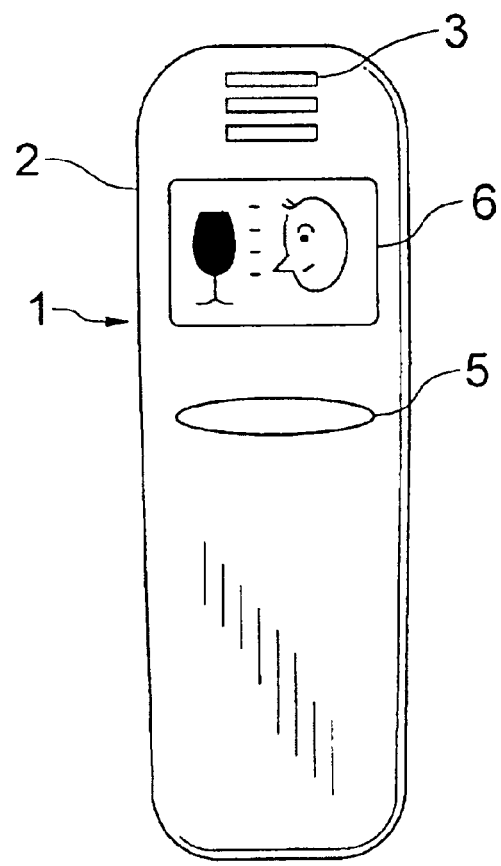
Figure 4B:
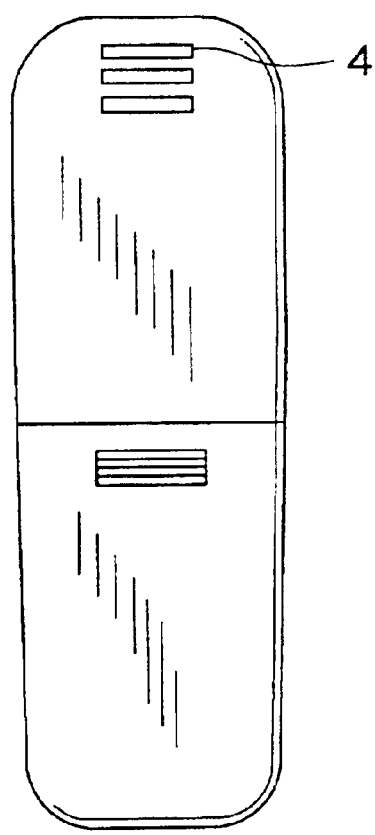
FIG. 4(b) is a rear view of the intoxication gauge.
Figure 5:
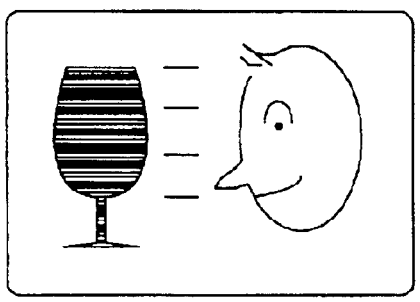
FIGS. 5(a) to (h) are graphic representations showing what different pictures appear to indicate the increasing degree of intoxication.
Figure 5:
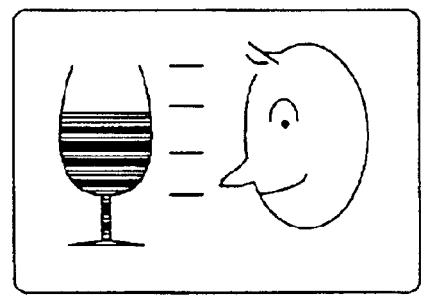
Figure 5:
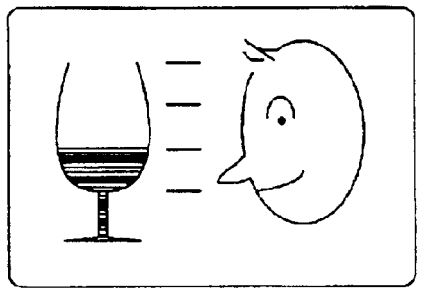
Figure 5:
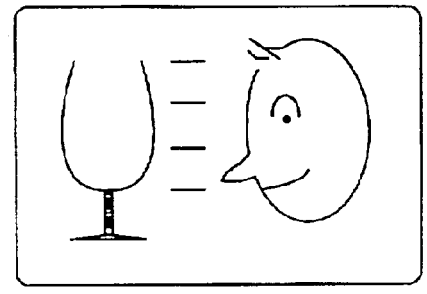
Figure 5:
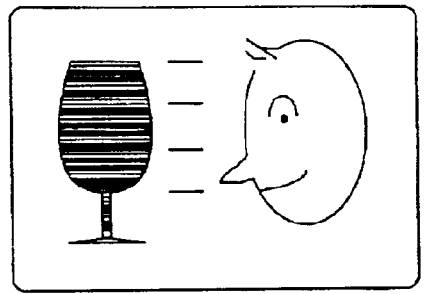
Figure 5:
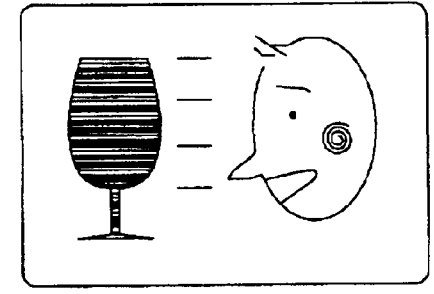
Figure 5:
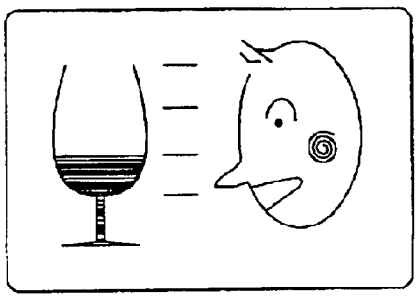
Figure 5:
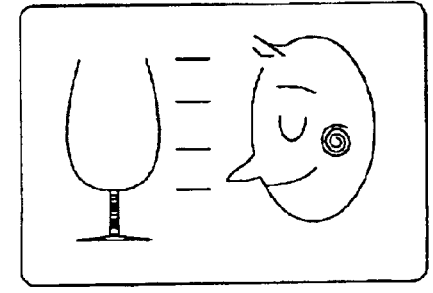

Referring to FIGS. 4 and 5, an exhalation gaseous component gauge is described as being applied to measuring the degree of intoxication. It uses an alcohol-sensitive semiconductor gas sensor, the ceramic insulator body of which is coated with tin oxide ($SnO_2$). The CPU is so programmed as to effect required arithmetic operation and control. Also, the CPU is so programmed as to permit the display device to give graphic representations of: the length of time left for the breath gauge to reach the standby position for measurement; degree of intoxication and other useful pieces of information such as the remaining amount of electricity in the battery.

The manner in which the breath test is made is described below:

First, the power switch 5 is depressed to put the power supply 7 in circuit with the components of the breath gauge 1, and then, a face and a glass filled with alcohol appear on the display 6 (see FIG. 5a). At the same time, a voltage is applied across the heater coil of the semiconductor gas sensor 10, thus effecting the thermal cleaning of the semiconductor gas sensor 10 and keeping it at a given constant temperature (standby position for measurement). The amount of the alcohol in the glass decreases with time, showing the length of time left for reaching the standby condition (see FIGS. 5a, 5b and 5c), and finally the empty glass appears at the time of finishing the thermal cleaning of the semiconductor sensor 10 (see FIG. 5d). Then, the user puts the breath gauge 1 close to his mouth to blow a breath into the exhalation taking-in slot 3.

The buzzer 8 responds to the signal from the semiconductor gas sensor 10 for making a continuous sound, thereby informing the user of the finishing of the required measurement. The CPU 9 makes a required calculation of the concentration of the ethyl alcohol relative to the breath to show the result of calculation on the display 6. The degree of intoxication is indicated in terms of the remaining amount of alcohol in the glass, which is given in terms of segments selected in the display 6.

Referring to FIGS. 5(e) to 5(h), the alcoholic concentration ranging from 0 to 0.09 mg/l (start) is indicated in terms of three graduations (see FIG. 5e); the alcoholic concentration ranging from 0.1 to 0.19 mg/l (noticeable intoxication) is indicated in terms of two graduations (see FIG. 5f); the alcoholic concentration ranging from 0.2 to 0.49 mg/l (significant intoxication) is indicated in terms of one graduation (see FIG. 5g); and the alcoholic concentration beyond 0.5 mg/l (strong intoxication) is indicated in terms of the empty glass (see FIG. 5h). Accordingly the remaing amount of liquid in the glass and the countenance change. Other appropriate pictures varying with the increasing degree of intoxication may be used.

The indication will automatically disappear in several seconds, thus finishing the measurement. If the battery is being exhausted, the empty glass appears and disappears in response,to depression of the power switch 5, thus informing the user of shortage of electricity in the battery 7.

Figure 6:
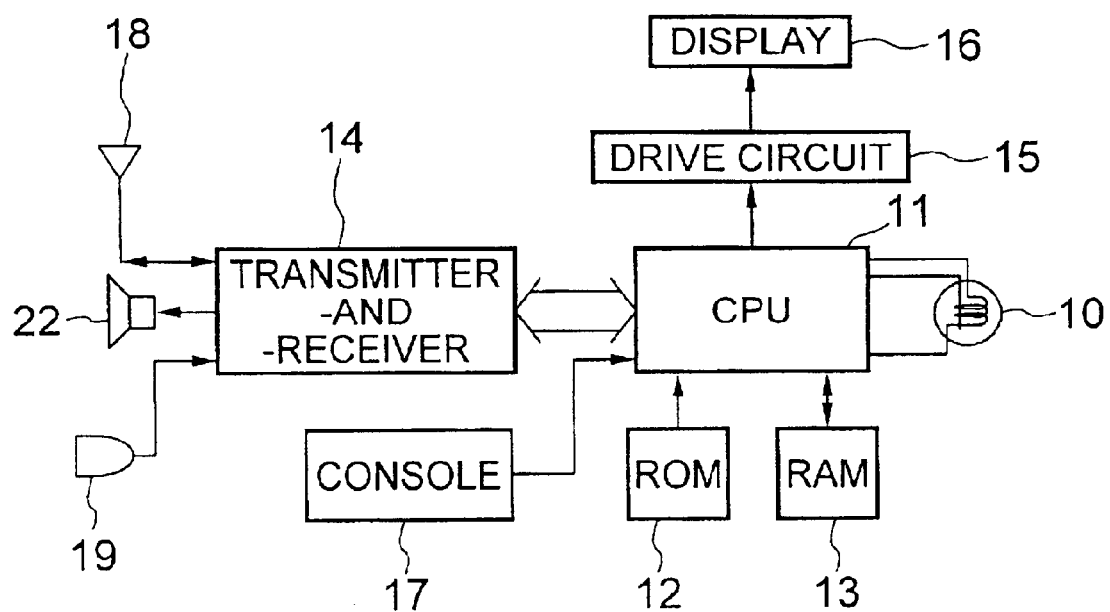
FIG. 6 is a block diagram showing a cellular phone equipped with function of measuring selected exhalation gaseous components according to the present invention.
Figure 7A:
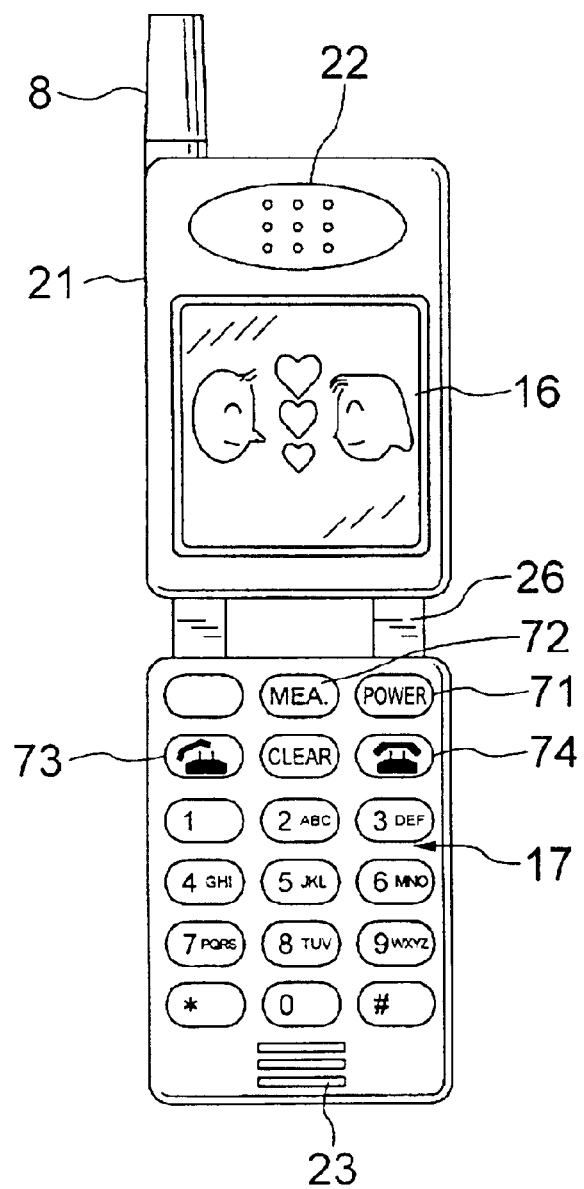
Figure 7B:
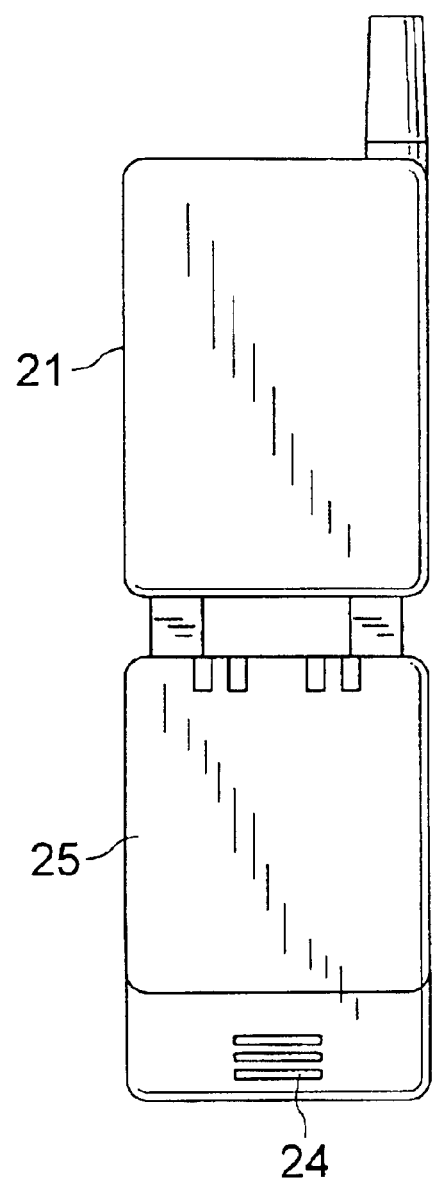
FIG. 7(b) is a rear view of the cellular phone equipped with the breath gauge.

FIGS. 6 and 7 show a cellular phone 21 equipped with function of measuring exhalation gaseous components. As shown in FIG. 6, the cellular phone comprises a CPU 11, associated ROM 12 and RAM 13, a transmitter-and-receiver circuit 14, a drive circuit 15, a liquid crystal display unit 16, a console 17 including push buttons 71, 72, 73 . . . , an antenna 18, a microphone 19, a receiver 22 and a semiconductor gas sensor 10. The CPU 1 effects required arithmetic operation and control according to different programs stored in the ROM 12 and data retrieved from the RAM 13, as for instance, signals transmitted and received can be processed in the transmitter-and-receiver circuit 14 under the control of the CPU 11. Specifically the voice-representative signal from the microphone 19 is converted to transmission signal in the transmitter-and-receiver circuit 14 to be transmitted via the antenna 8. When the signal arrives at the antenna 18, it is converted to the voice-representative signal in the transmitter-and-receiver circuit 14 to be directed to the receiver 22.

The liquid crystal display 16 is connected to the CPU 11 via the drive circuit 15 to show the results of arithmetic operations and other processings effected by the CPU 11 as for instance follows: the telephone number and the name of the person who is calling are displayed. Required pieces of information can be inputted by depressing selected push buttons in the console 17.

The cellular phone 21 is descried as being equipped with function of measuring the degree of foul breath. As seen from FIG. 7, the palm-sized foldable casing is composed of two parts hinged at 26. One part of the foldable casing has a display unit 6 and a receiver 22 fixed thereon whereas the other part has a console 17 including a plurality of push buttons 71, 72, 73 - - - provided on its front side, and a detachable battery pack 25 attached to its rear side. In addition, the other part of the foldable casing has exhalation taking-in and taking-out slots 23 and 24 made on its front and rear sides respectively. The semiconductor gas sensor 10 is so placed as to permit the breath out of one's mouth to flow over the semiconductor gas sensor 10 on the way from the exhalation taking-in slot 23 to the exhalation taking-out slot 24. The exhalation taking-in slot 23 may be used as a part of mouth piece or speaker 19.

The display device 6 gives graphic representations showing the result of measurement, the length of time left for putting the exhalation gauge in its standby condition for measurement, the remaining quantity of electricity available from the battery and other useful pieces of information.

The halitosis-sensitive semiconductor gas sensor 10 for indicating the degree of smelling bad in someone's breath is a ceramic insulator body coated with a semiconductor material of tin oxide ($SnO_2$), and the ceramic insulator body has a heater coil contained therein.

The CPU 11 of the cellular phone 21 is so programmed as to determine the quantity of the foul breadth components detected by the sensor and to allow the display device 16 of the cellular phone 21 to show the so determined quantity of the foul breadth components. In addition, the ROM 12 and RAM 13 associated with the CPU 11 store programs and data required for controlling and performing necessary operations in the mode of determining the degree of foul breath, as described later in detail. The cellular phone 21 may include further a buzzer (not shown) connected to the CPU 11, thus permitting the buzzer to respond to detection of the exhalation by the semiconductor gas sensor 11 for informing a person of detection of the exhalation.

In use, the start button is depressed to permit the thermal cleaning of the semiconductor gas sensor 10 to start, thus putting the gauge in its standby position. Then, the user gives a breath to the exhalation taking-in slot 23 to cause the electric resistance of the semiconductor gas sensor 10 to vary, thus permitting detection of the breath. In response to the detection of the breath the electric current flowing the heater of the semiconductor gas sensor is lowered, and at the same time the electric resistance is determined. The ratio of the so determined resistance (post-temperature descent) relative to the resistance (pre-temperature descent) is compared with a set value to determine the degree of foul breath, which is given in the display Also, it is possible to effect an exhalation measurement while speaking to the person at the other end of line. The cellular phone may be so modified as to start the thermal cleaning in response to depression of the communication start button, thus permitting the required measurement of the exhalation during telephone conversation. The result of measurement thus made is given in the display 16. The remaining amount of electricity available from the battery pack 25 is watched all the time, and the remaining electricity is allotted preferentially to the communication.

Figure 8:
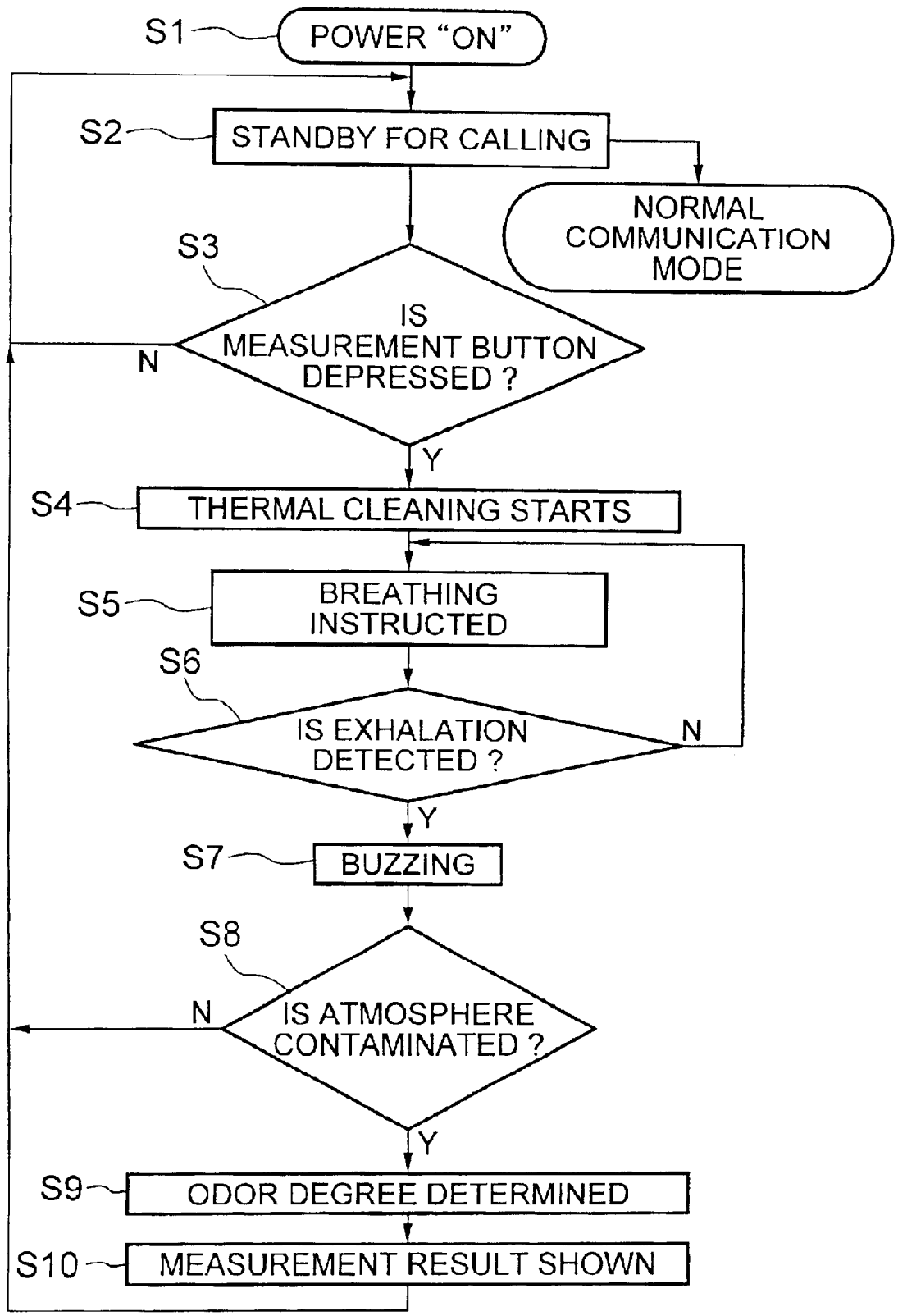
FIG. 8 is a flowchart showing how the degree of unpleasant odor can be determined.

Referring to FIG. 8, the proceeding of exhalation measurement is described below.

Usually the cellular phone 21 is kept in its standby position for receiving a call from another mobile station by turning the power supply on. If not, the power button 71 is depressed to put the power supply in circuit with selected parts of the cellular phone (STEP 1), thus putting the cellular phone 21 in its standby position (STEP 2). Then, the measurement button 72 is depressed to effect the thermal cleaning of the semiconductor gas sensor 10 for a predetermined length of time by applying a relatively high voltage across the heater coil of the gas sensor 10, thereby removing particles of foreign substance or water from the sensor's surface (STEPs 3 and 4). Such pulverized foreign substance and water are apt to be deposited on the sensor's surface while the sensor has not been used a relatively elongated length of time, and their presence on the sensor will cause an adverse effect on measurement. Thus, the sensor remains at a raised temperature.

The user is being informed as to how long he must wait for the standby position reached by the breath gauge from the numeral varying with time in the display, as for instance, 5→4→3→2→1

When the thermal cleaning has been finished, "0" and "give a breath to the exhalation taking-in slot;" appear in the display (STEP 5). The user puts his mouth close to the exhalation taking-in slot 23 to give a breath thereto. This posture looks like using his cellular phone, and therefore, nobody would realize that he is measuring the degree of foul breath.

The CPU 11 responds to the signal from the gas sensor 10 (STEP 6) for allowing the speaker to make a warning sound, thereby informing the user of detection of his breath (STEP 7). Subsequent to the detection the CPU 11 makes a decision as to whether or not the surrounding atmosphere is contaminated, and in the affirmative case the proceeding is made to cease (STEP 8); no correct measurement is possible. When the methyl mercaptan-and-ethylene mixture gas is burnt on the heated gas sensor 10, the electric resistance of the gas sensor 10 is lowered, accordingly increasing the electric current flowing therethrough. The CPU 11 determines the electric resistance from the increased electric current to compare the so determined electric resistance with the reference value. Thus, the concentration of the mixture gas can be determined (STEP 9). The measurement result is given in the display 16 (See FIGS. 3e to 3h).

The measurement result disappears automatically in several seconds, thus finishing the measurement proceeding to allow the cellular phone to return to its initial standby position for receiving a call from another mobile station (STEP 10).

Figure 9:
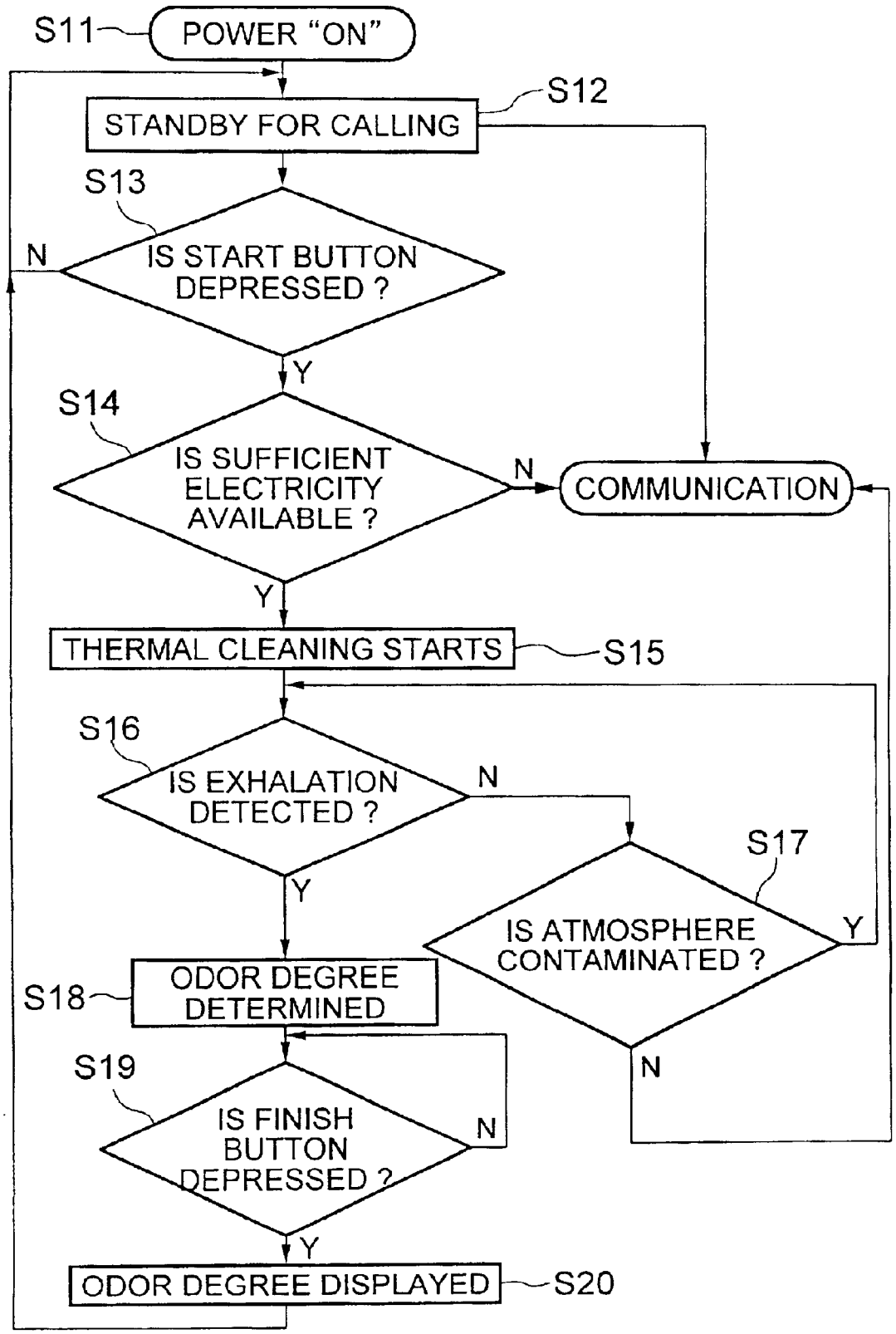
FIG. 9 is another flowchart showing how the degree of unpleasant odor can be determined.

Referring to FIG. 9, the manner in which the cellular phone 21 permits exhalation measurement while speaking to the person at the other, end of line is described.

First, the power button 71 is depressed to put the power supply 25 in circuit with selected parts of the cellular phone (STEP 11), thus putting the cellular phone in its standby position for receiving a call from another mobile station (STEP 12). No matter in which direction a call may be made, the start button 73 is depressed, and then, the preceding of exhalation measurement automatically starts (STEP 13). Prior to depression of the start button 73 the cellular phone 21 remains in its standby position for receiving a call from another mobile station.

Then, the remaining amount of electricity available from the battery pack 25 is checked (STEP 14). If the battery pack 25 is shortage of electricity, the remaining amount of electricity is allotted to telephone use preferential to the exhalation measurement, which must be made to cease.

If the battery pack 25 affords to allow the exhalation measurement to be made, the thermal cleaning of the semiconductor gas sensor 10 is effected a predetermined length of time by applying a relatively high voltage across the heater coil of the sensor 10, thereby removing particles of foreign substance or water from the sensor's surface (STEP 15). The measurement cannot be begun before finishing the thermal cleaning. No information as to how long the thermal cleaning may last is given in the display 16. Even if such an information were given in the display 16, the user could not have a look at the display; he puts his cellular phone close to his mouth.

Thereafter, the temperature of the gas sensor 10 is lowered to the normal temperature at which the measurement is effected, and the measurement is actually effected when the gas sensor 10 has been stable in condition.

The communication is effected all the time, but the description of the communication proceeding is omitted.

The cellular phone remains in the standby position for detecting when the breath flows over the gas sensor 10

(STEP 16). This is because the user while listening to the person at the other end of line cannot utter any words, so that the cellular phone may wait for his turn for uttering and breathing. If no exhalation is detected for a relatively long period, a decision is made as to whether the surrounding atmosphere is contaminated or not, and in the affirmative case the exhalation measurement is made to cease (STEP 17), thus allowing the cellular phone to effect ordinary communication only. This is because nobody can say how the surrounding condition is like when receiving a call from another mobile station. In the negative case the cellular phone is allowed to return to its standby position for detection of exhalation (STEP 16).

The methyl mercaptan-and-ethylene mixture gas on his breath is deposited and burnt on the heated gas sensor 10 to reduce the electric resistance, and then, the concentration of the mixture gas can be estimated in terms of electric resistance (STEP 18). After the end of telephone communication the user depresses the finish button 74 (STEP 19), and then the measurement result appears on the display (STEP 20). Thus, the exhalation measurement ends, allowing the cellular phone to return to its standby position for receiving a call from another mobile station.

The CPU 11 may use a variety of software for providing different functions in measuring the degree of foul breath as for instances, follows:

the user may have a choice between the mode in which an exhalation measurement is automatically effected in response to every call from another mobile station and the mode in which an exhalation measurement is effected at the user's request;

in case that no exhalation is detected within a predetermined length of time, the cellular phone is forcedly switched to the communication mode only, thereby saving the electricity in the battery pack;

no matter how many times the exhalation measurement may be repeated during telephonic conversation, the last measurement result is displayed, thereby informing the user of the degree of foul breadth caused by the long-termed telephonic conversation;

the exhalation measurement is permitted in a predetermined length of time, say, in ten minutes after start of telephonic conversation; and the exhalation measurement starts just prior to the presumable end of telephonic conversation, which is assumed from the length of time taken for the last telephonic conversation, the average length of time estimated from the historical recordings of telephonic conversations or the length of time which can be most probably taken when speaking to a particular person who can be identified from his or her telephone number.

The invention is described as being applied to a foldable cellular phone, which facilitates the exhalation measurement, provided that the exhalation taking-in slot is made in the vicinity of its mouth piece in the form of slots 23. No matter what shape the cellular phone may have, it suffices that its configuration permits the user to put his mouth close to the gas sensor, or that the breath may be redirected to the gas sensor by using his hand.

The semiconductor gas sensor is described as being sensitive to foul breath. Alternatively an alcohol-sensitive semiconductor gas sensor may be used, thereby giving an indication of the degree of intoxication. Also, the exhalation gaseous component gauge and the cellular phone equipped with function of determining the exhalation gaseous components may be modified by changing their semiconductor gas sensors to detect any body odor other than foul breath, such as hircismus, foot odor, menstrual odor or the incontinence of urine.

As for pictures given in the display to show the degree of bad breath or intoxication the picture of faces varies with the increasing degree of measurement. Specifically the countenance is pleasing less and less in determining the increasing degree of bad breath, and the face turns redness increasingly with the increasing degree of intoxication. Such pictures are easily understandable in association with the incident. Likewise, examples of pictures to show the degree of any body odor measurement as referred to above are: a human shape stands upright in the display for the normal condition; the human shape crouches for the unwholesome condition; and the human shape lies for the worst condition.

What claimed is:

1. An exhalation gaseous component gauge including, in a palm-sized casing having exhalation taking-in and taking-out slots on its front and rear sides respectively, at least an electric power supply, a CPU connected to the power supply via an associated switch, a gas sensor connected to the CPU and a display device fixed to the front side of the casing, and connected to the CPU, characterized in that the gas sensor is located to permit the breath out of one's mouth to flow over the gas sensor on the way from the exhalation taking-in slot to the exhalation taking-out slot, and the palm-sized casing is sized and configured to permit one to have a look at the display while holding the gauge in a hand to direct the breath from one's mouth to the exhalation taking-in slot;

further comprising a buzzer connected to the CPU, for permitting the buzzer to respond to detection of a halitosis detectable quantity of exhalation by the gas sensor for informing a person of detection of such exhalation.

2. A cellular phone equipped with a function of measuring halitosis components characterized in that a palm-sized cellular phone casing has exhalation taking-in and taking-out slots on its front and rear sides respectively, and a gas sensor is placed in the casing to permit the breath out of one's mouth to flow over the gas sensor on the way from the exhalation taking-in slot to the exhalation taking-out slot, the CPU of the cellular phone being connected to the gas sensor, and being programmed to determine the quantity of the halitosis components detected by the sensor and to allow the display device of the cellular phone to indicate the so determined quantity of the halitosis components.

3. A cellular phone equipped with function of measuring exhalation gaseous components according to claim 2 wherein it further includes a buzzer connected to the CPU, for permitting the buzzer to respond to detection of a halitosis detectable quantity of exhalation by the gas sensor for informing a person of detection of such exhalation.

4. A cellular phone equipped with function of measuring exhalation gaseous components according to claim 2 wherein the CPU is so programmed as to permit the display device to show pictures varying with the detected component quantities.

5. A cellular phone equipped with function of measuring exhalation gaseous components according to claim 2 wherein the semiconductor gas sensor has halitosis-sensitive characteristics, thereby giving an indication of the degree of smelling bad in someone's breath.

6. A cellular phone equipped with function of measuring exhalation gaseous components according to claim 5 wherein the pictures show countenances varying with the detected component quantities.

7. A cellular phone equipped with function of measuring exhalation gaseous components according to claim 2 wherein the pictures indicate the remaining liquid amount in a glass and/or countenances or postures varying with the detected component quantities.

8. A cellular phone equipped with function of measuring exhalation gaseous components according to claim 2 wherein the CPU is so programmed as to permit the display device to give graphic representations of the length of time left for the gauge to reach the standby position for measurement.

9. An exhalation gaseous component gauge including, in a palm-sized casing having exhalation taking-in and taking-out slots made on its front and rear sides respectively, at least an electric power supply, a CPU connected to the power supply via an associated switch, a gas sensor connected to the CPU and a display device fixed to the front side of the casing, and connected to the CPU, characterized in that the gas sensor being so placed as to permit the breath out of one's mouth to flow over the gas sensor on the way from the exhalation taking-in slot to the exhalation taking-out slot, the palm-sized casing being so sized and configured as to permit one to have a look at the display while holding the gauge in hand to direct the breath from one's mouth to the exhalation taking-in slot, and that the CPU is so programmed as to permit the display to show pictures of remaining liquid amount in a glass and/or postures varying with the detected component quantities.

10. A cellular phone equipped with function of measuring exhalation gaseous components characterized in that a palm-sized cellular phone casing has exhalation taking-in and taking-out slots made on its front and rear sides respectively, and that a gas sensor is so placed in the casing as to permit the breath out of one's mouth to flow over the gas sensor on the way from the exhalation taking-in slot to the exhalation taking-out slot, the CPU of the cellular phone being connected to the gas sensor, and being so programmed as to determine the quantity of the exhalation gaseous components detected by the sensor and to allow the display device of the cellular phone to indicate the so determined quantity of the exhalation gaseous components, and that the CPU is so programmed as to permit the display to show pictures of countenance varying with the detected component quantities.

11. A cellular phone equipped with function of measuring exhalation gaseous components characterized in that a palm-sized cellular phone casing has exhalation taking-in and taking-out slots made on its front and rear sides respectively, and that a gas sensor is so placed in the casing as to permit the breath out of one's mouth to flow over the gas sensor on the way from the exhalation taking-in slot to the exhalation taking-out slot, the CPU of the cellular phone being connected to the gas sensor, and being so programmed as to determine the quantity of the exhalation gaseous components detected by the sensor and to allow the display device of the cellular phone to indicate the so determined quantity of the exhalation gaseous components, and that the CPU is so programmed as to permit the display to show pictures of remaining liquid amount in a glass and/or postures varying with the detected component quantities.

12. A cellular phone equipped with function of measuring exhalation gaseous components characterized in that a palm-sized cellular phone casing has exhalation taking-in and taking-out slots made on its front and rear sides respectively, and that a gas sensor is so placed in the casing as to permit the breath out of one's mouth to flow over the gas sensor on the way from the exhalation taking-in slot to the exhalation taking-out slot, the CPU of the cellular phone being connected to the gas sensor, and being so programmed as to determine the quantity of the exhalation gaseous components detected by the sensor and to allow the display device of the cellular phone to indicate the so determined quantity of the exhalation gaseous components, and that the CPU is so programmed as to permit the display to show simple pictures presumable in association with the incident relating to the exhalation to be detected, which simple pictures are given in terms of number varying with the detected component quantities.

* * * * *